(12) United States Patent
Ben Zriham et al.

(10) Patent No.: US 9,421,061 B2
(45) Date of Patent: Aug. 23, 2016

(54) VENTRICULAR FAR FIELD REDUCTION

(71) Applicant: BIOSENSE WEBSTER (ISRAEL) LTD., Yokneam (IL)

(72) Inventors: Yaniv Ben Zriham, Binyamina (IL); Roy Urman, Karkur (IL); Meir Bar-Tal, Haifa (IL); Richard P. M. Houben, Lanaken (BE)

(73) Assignee: Biosense Webster (Israel) Ltd., Yokneam (IL)

( * ) Notice: Subject to any disclaimer, the term of this patent is extended or adjusted under 35 U.S.C. 154(b) by 8 days.

(21) Appl. No.: 14/574,578

(22) Filed: Dec. 18, 2014

(65) Prior Publication Data

US 2016/0175023 A1 Jun. 23, 2016

(51) Int. Cl.
| A61B 5/0456 | (2006.01) |
| A61B 18/12 | (2006.01) |
| A61B 5/0472 | (2006.01) |
| A61B 5/04 | (2006.01) |
| A61B 18/00 | (2006.01) |

(52) U.S. Cl.
CPC ......... *A61B 18/1206* (2013.01); *A61B 5/04012* (2013.01); *A61B 5/0456* (2013.01); *A61B 5/0472* (2013.01); *A61B 2018/00023* (2013.01); *A61B 2018/00351* (2013.01); *A61B 2018/00577* (2013.01); *A61B 2018/00642* (2013.01); *A61B 2018/00702* (2013.01); *A61B 2018/00839* (2013.01)

(58) Field of Classification Search
CPC ............. A61B 5/04012; A61B 5/0456; A61B 5/04525
See application file for complete search history.

(56) References Cited

U.S. PATENT DOCUMENTS

| 5,546,951 | A | 8/1996 | Ben Haim |
| 6,226,542 | B1 | 5/2001 | Reisfeld |
| 6,301,496 | B1 | 10/2001 | Reisfeld |
| 6,669,692 | B1 | 12/2003 | Nelson et al. |
| 6,690,963 | B2 | 2/2004 | Ben Haim |
| 6,892,091 | B1 | 5/2005 | Ben Haim |
| 2014/0005664 | A1 | 1/2014 | Govari |
| 2014/0187991 | A1* | 7/2014 | Thakur ................ A61B 5/6858 600/521 |

FOREIGN PATENT DOCUMENTS

WO WO 96/05768 A1 2/1996

* cited by examiner

*Primary Examiner* — George Evanisko
(74) *Attorney, Agent, or Firm* — Louis J. Capezzuto

(57) ABSTRACT

Far field reduction is carried out in a cardiac electrogram by extracting unipolar beats of an intracardiac electrogram that occur within a predetermined time interval that includes QRS peaks, constructing a first mean unipolar beat by averaging the extracted unipolar beats, and accepting unipolar beats that cross-correlate with the first mean unipolar beat. A second mean unipolar beat is constructed from the accepted unipolar beats. A ventricular far field component is determined from the extracted unipolar beats and subtracted from the intracardiac electrogram to distinguish a local component of the intracardiac electrogram.

16 Claims, 8 Drawing Sheets

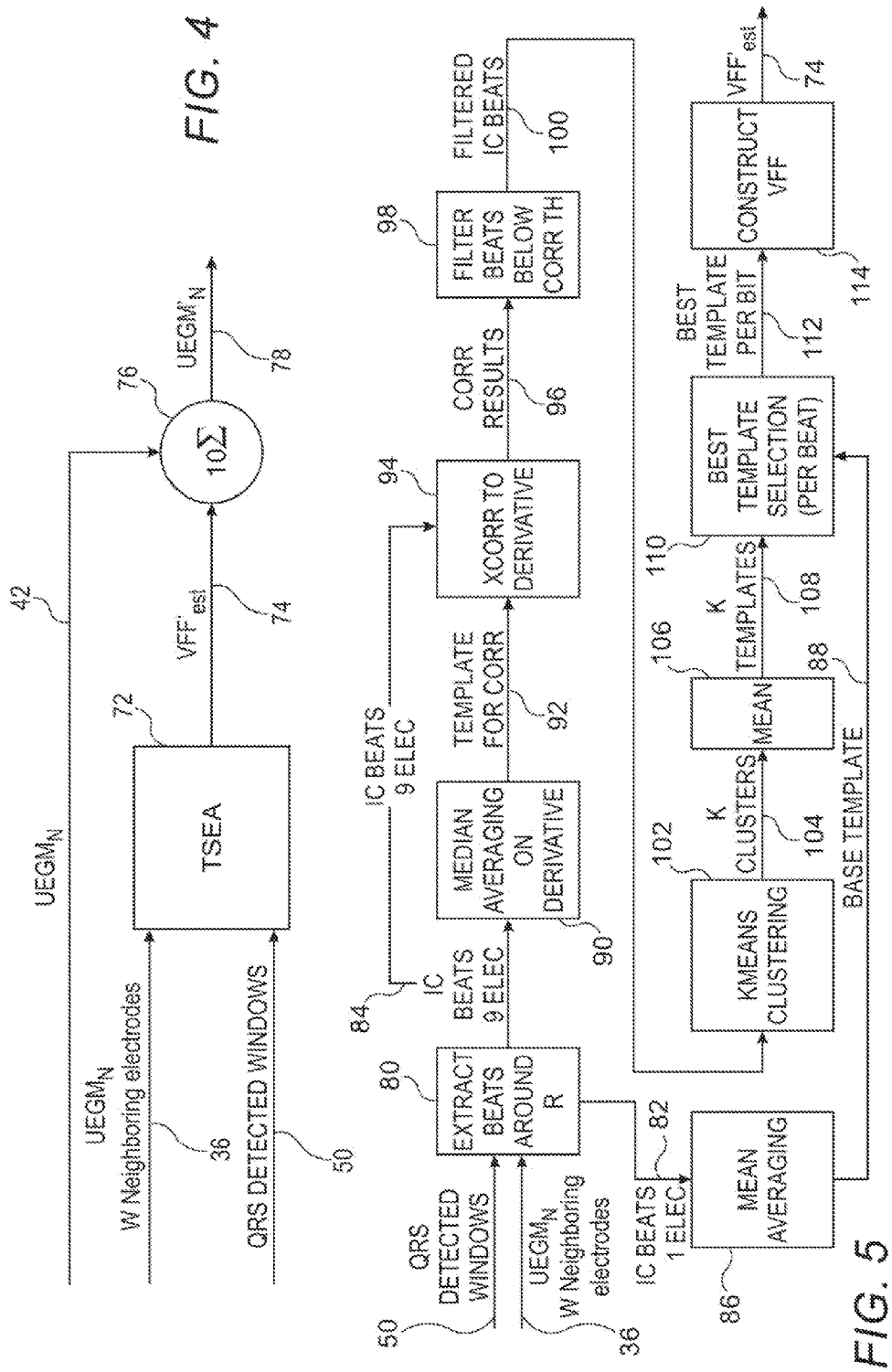

VENTRICULAR FAR FIELD REDUCTION

BACKGROUND OF THE INVENTION

1. Field of the Invention

This invention relates to cardiac physiology. More particularly, this invention relates to the evaluation of electrical propagation in the heart.

2. Description of the Related Art

The meanings of certain acronyms and abbreviations used herein are given in Table 1.

TABLE 1

| Acronyms and Abbreviations | |
| --- | --- |
| BSECG | Body Surface ECG |
| ECG | Electrocardiogram |
| EGM | Electrogram |
| TEA | Time Ensemble Averaging |
| UEGM | Unipolar Electrogram |
| VFF | Ventricular Far Field |

Cardiac arrhythmias such as atrial fibrillation are an important cause of morbidity and death. Commonly assigned U.S. Pat. No. 5,546,951, and U.S. Pat. No. 6,690,963, both issued to Ben Haim and PCT application WO 96/05768, all of which are incorporated herein by reference, disclose methods for sensing an electrical property of heart tissue, for example, local activation time, as a function of the precise location within the heart. Data are acquired with one or more catheters having electrical and location sensors in their distal tips, which are advanced into the heart. Methods of creating a map of the electrical activity of the heart based on these data are disclosed in commonly assigned U.S. Pat. No. 6,226,542, and U.S. Pat. No. 6,301,496, both issued to Reisfeld, which are incorporated herein by reference. As indicated in these patents, location and electrical activity is typically initially measured on about 10 to about 20 points on the interior surface of the heart. These data points are then generally sufficient to generate a preliminary reconstruction or map of the cardiac surface. The preliminary map is often combined with data taken at additional points in order to generate a more comprehensive map of the heart's electrical activity. Indeed, in clinical settings, it is not uncommon to accumulate data at 100 or more sites to generate a detailed, comprehensive map of heart chamber electrical activity. The generated detailed map may then serve as the basis for deciding on a therapeutic course of action, for example, tissue ablation, to alter the propagation of the heart's electrical activity and to restore normal heart rhythm.

Catheters containing position sensors may be used to determine the trajectory of points on the cardiac surface. These trajectories may be used to infer motion characteristics such as the contractility of the tissue. As disclosed in U.S. Pat. No. 5,738,096, issued to Ben Haim, which is incorporated herein in its entirety by reference, maps depicting such motion characteristics may be constructed when the trajectory information is sampled at a sufficient number of points in the heart.

Electrical activity at a point in the heart is typically measured by advancing a multiple-electrode catheter to measure electrical activity at multiple points in the heart chamber simultaneously. A record derived from time varying electrical potentials as measured by one or more electrodes is known as an electrogram. Electrograms may be measured by unipolar or bipolar leads, and are used, e.g., to determine onset of electrical propagation at a point, known as local activation time.

Sensors in a cardiac chamber may detect far-field electrical activity, i.e., the ambient electrical activity originating away from the sensors, which can distort or obscure local electrical activity, i.e., signals originating at or near the sensor location. Commonly assigned U.S. Patent Application Publication No. 2014/0005664 of Govari et al., which is herein incorporated by reference, discloses distinguishing a local component in an intracardiac electrode signal, due to the tissue with which the electrode is in contact from a remote-field contribution to the signal, and explains that a therapeutic procedure applied to the tissue can be controlled responsively to the distinguished local component.

U.S. Patent Application Publication No. 2014/0187991 of Thakur et al. proposes a method for mapping a cardiac chamber by sensing activation signals of intrinsic physiological activity with a plurality of electrodes disposed in or near the cardiac chamber. The method includes isolating R-wave events in the activation signals, generating a far-field activation template representative of a far-field activation signal component based on the R-wave events, and filtering the far-field activation template from the activation signals to identify near-field activation signal components in the activation signals.

SUMMARY OF THE INVENTION

There is provided according to embodiments of the invention a method of far field reduction, which is carried out by detecting peaks of a QRS complex of a cardiac electrogram, extracting unipolar beats of an intracardiac electrogram that occur within a predetermined time interval that includes respective detected peaks, constructing a first mean unipolar beat by averaging the extracted unipolar beats, cross correlating the extracted unipolar beats with the first mean unipolar beat by determining respective time-lags therebetween, and accepting ones of the extracted unipolar beats wherein a cross correlation thereof exceeds a predetermined correlation threshold. The method is further carried out by constructing a second mean unipolar beat from the accepted unipolar beats, determining a ventricular far field component by subtracting the second mean unipolar beat from the extracted unipolar beats, subtracting the ventricular far field component from the intracardiac electrogram to distinguish a local component of the intracardiac electrogram, and controlling a medical procedure responsively to the local component.

According to an aspect of the method, the predetermined correlation threshold includes a time lag that does not exceed 10 ms.

According to another aspect of the method, the predetermined correlation threshold includes a difference between peak amplitudes of the extracted unipolar beats and the first mean unipolar beat that does not exceed 10 percent.

According to a further aspect of the method, constructing a first mean unipolar beat includes computing a median derivative beat by differentiating the extracted unipolar beats, and cross correlating is performed between the extracted unipolar beats and the median derivative beat.

According to one aspect of the method, constructing a second mean unipolar beat includes aligning the extracted unipolar beats.

According to yet another aspect of the method, constructing a second mean unipolar beat includes dividing the accepted unipolar beats into a plurality of clusters, and constructing respective cluster-specific mean unipolar beats for each of the clusters.

According to an additional aspect of the method, dividing the accepted unipolar beats is performed by k-means clustering according to Euclidean distances between the accepted unipolar beats.

According to still another aspect of the method, determining a ventricular far field component includes selecting an optimum one of the cluster-specific mean unipolar beats for respective accepted unipolar beats, and subtracting the selected cluster-specific mean unipolar beats from the extracted unipolar beats.

There is further provided according to embodiments of the invention an apparatus, including an intra-body probe, the probe being adapted to contact tissue in a heart, a display, and a processor. The processor is configured to receive an electrical signal from an electrode of the probe, to distinguish a local component of the signal that is due to the tissue with which the electrode is in contact from a remote-field contribution to the signal by performing the steps of: detecting peaks of a QRS complex of a cardiac electrogram, extracting unipolar beats of an intracardiac electrogram received via the electrode, wherein the extracted unipolar beats occur within a predetermined time interval that includes respective detected peaks, constructing a first mean unipolar beat by averaging the extracted unipolar beats, cross correlating the extracted unipolar beats with the first mean unipolar beat by determining respective time-lags therebetween, accepting ones of the extracted unipolar beats wherein a cross correlation thereof exceeds a predetermined correlation threshold, constructing a second mean unipolar beat from the accepted unipolar beats, determining a ventricular far field component by subtracting the second mean unipolar beat from the extracted unipolar beats, subtracting the ventricular far field component from the intracardiac electrogram to distinguish the local component of the intracardiac electrogram, and outputting the local component to the display.

There is further provided according to embodiments of the invention a method which is carried out by inserting a probe into a heart of a subject. A unipolar intracardiac electrode is disposed on the distal segment of the probe. The method is further carried out by concurrently receiving an intracardiac electrogram from a location in the heart with the intracardiac electrode and receiving another electrogram with a second electrode, forming a first template by averaging beats of the intracardiac electrogram in alignment with R-wave complexes of the other electrogram, computing respective correlations between the beats of the intracardiac electrogram and the first template, selecting beats of the intracardiac electrogram, wherein the respective correlations thereof exceed a predetermined value, forming a second template from the selected beats of the intracardiac electrogram, generating, based on the second template, a signal representing a far field component of the intracardiac electrogram, removing the far field component from the intracardiac electrogram to yield a filtered intracardiac electrogram, and reporting the filtered intracardiac electrogram.

According to yet another aspect of the method, forming a second template includes dividing the selected beats of the intracardiac electrogram into a plurality of clusters, and constructing a plurality of cluster-specific second templates for each of the clusters.

According to still another aspect of the method, dividing the selected beats of the intracardiac electrogram is performed by k-means clustering according to Euclidean distances between the selected beats.

According to a further aspect of the method, generating includes selecting an optimum one of the cluster-specific second templates for respective selected beats, and subtracting the optimum template from the selected beats, respectively.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein:

FIG. 4 is a block diagram illustrating removal of ventricular far field effects from intracardiac unipolar channels, in accordance with an alternate embodiment of the invention;

FIG. 5 is a detailed block diagram of the TEA algorithm shown in FIG. 4 in accordance with an alternate embodiment of the invention.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily needed for practicing the present invention. In this instance, well-known circuits, control logic, and the details of computer program instructions for conventional algorithms and processes have not been shown in detail in order not to obscure the general concepts unnecessarily.

System Overview

Figure 1:
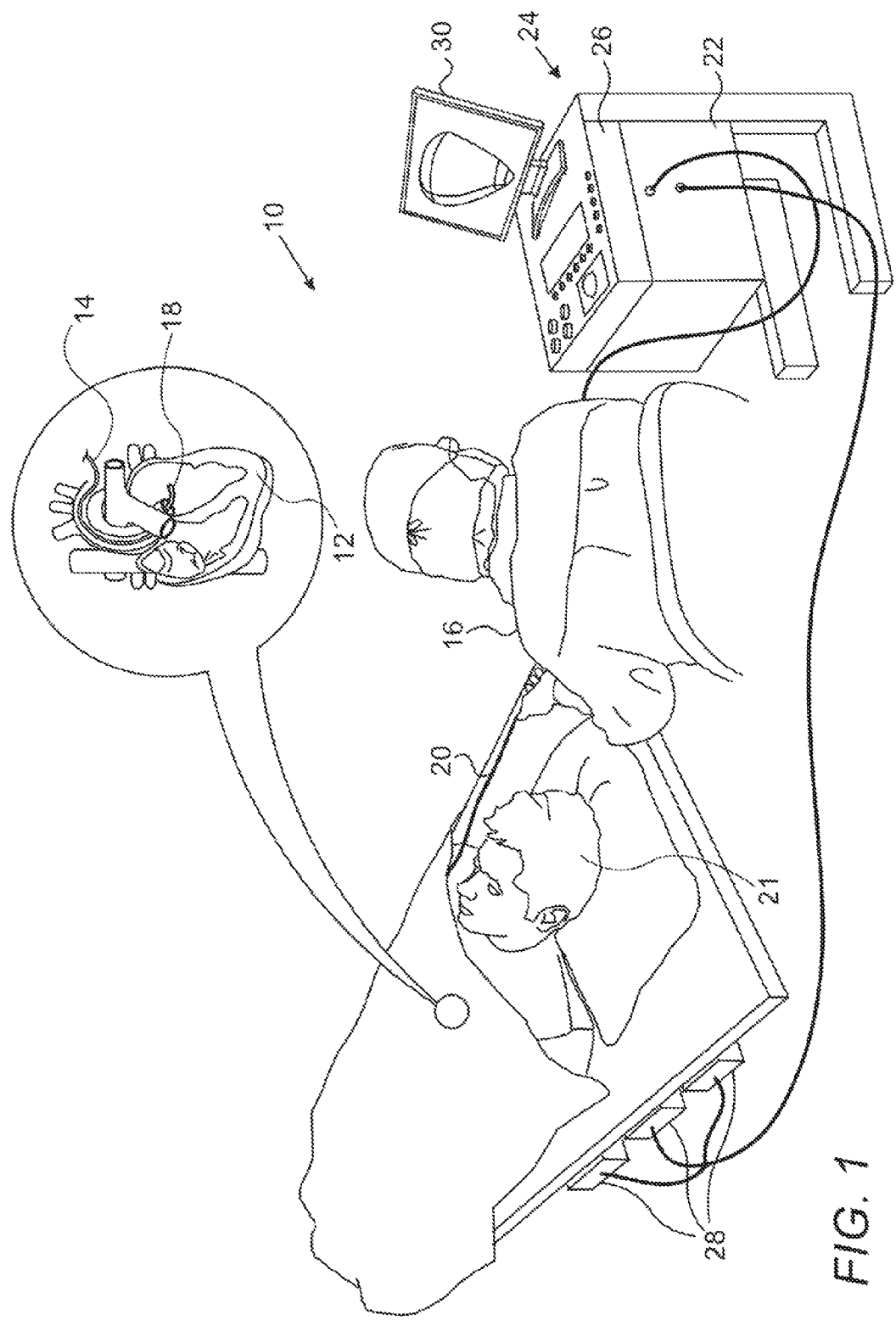
FIG. 1 is a pictorial illustration of a system for detecting electrical activity in a heart of a living subject in accordance with an embodiment of the invention.

Turning now to the drawings, reference is initially made to FIG. 1, which is a pictorial illustration of a system 10 for detecting areas of electrical activity in a heart 12 of a living subject 21 in accordance with a disclosed embodiment of the invention. The system comprises a probe, such as a catheter 14, which is percutaneously inserted by an operator 16, who is typically a physician, through the patient's vascular system into a chamber or vascular structure of the heart. The operator 16 brings the catheter's distal tip 18 into contact with the heart wall at a target site that is to be evaluated. Unipolar and bipolar electrograms are recorded using mapping electrodes on the distal segment of the catheter. Electrical activation maps based on the electrograms are then prepared, according to the methods disclosed in the above-noted U.S. Pat. Nos. 6,226,542, and 6,301,496, and in commonly assigned U.S. Pat. No. 6,892,091, whose disclosure is herein incorporated by reference.

The system 10 may comprise a general purpose or embedded computer processor, which is programmed with suitable software for carrying out the functions described hereinbelow. Thus, although portions of the system 10 shown in other drawing figures herein are shown as comprising a number of separate functional blocks, these blocks are not necessarily separate physical entities, but rather may represent, for example, different computing tasks or data objects stored in a memory that is accessible to the processor. These tasks may be carried out in software running on a single processor, or on multiple processors. The software may be provided to the processor or processors on tangible non-transitory media, such as CD-ROM or non-volatile memory. Alternatively or additionally, the system 10 may comprise a digital signal processor or hard-wired logic.

The catheter 14 typically comprises a handle 20, having suitable controls on the handle to enable the operator 16 to steer, position and orient the distal end of the catheter as desired to the ablation. To aid the operator 16, the distal portion of the catheter 14 contains position sensors (not shown) that provide signals to a positioning processor 22, located in a console 24. The catheter 14 may be adapted, mutatis mutandis, from the ablation catheter described in commonly assigned U.S. Pat. No. 6,669,692, whose disclosure is herein incorporated by reference. The console 24 typically contains an ECG processor 26 and a display 30.

The positioning processor 22 measures location and orientation coordinates of the catheter 14. In one embodiment, the system 10 comprises a magnetic position tracking system that determines the position and orientation of the catheter 14. The system 10 typically comprises a set of external radiators, such as field generating coils 28, which are located in fixed, known positions external to the patient. The coils 28 generate electromagnetic fields in the vicinity of the heart 12. These fields are sensed by magnetic field sensors located in the catheter 14.

Typically, the system 10 includes other elements, which are not shown in the figures for the sake of simplicity. For example, the system 10 may include an electrocardiogram (ECG) monitor, coupled to receive signals from one or more body surface electrodes, to provide an ECG synchronization signal to the console 24. The system 10 typically also includes a reference position sensor, either on an externally-applied reference patch attached to the exterior of the subject's body, or on an internally-placed catheter, which is inserted into the heart 12 maintained in a fixed position relative to the heart 12. Conventional pumps and lines for circulating liquids through the catheter 14 for cooling an ablation site may be provided.

One system that embodies the above-described features of the system 10 is the CARTO® 3 System, available from Biosense Webster, Inc., 3333 Diamond Canyon Road, Diamond Bar, Calif. 91765. This system may be modified by those skilled in the art to embody the principles of the invention described herein. Multi-electrode basket and spline catheters are known that are suitable for obtaining unipolar and bipolar electrograms. An example of such a spline catheter is the Pentaray® NAV catheter, available from Biosense Webster.

Ventricular Far Field Cancelation

First Embodiment

One embodiment of a time ensemble averaging (TEA) algorithm for removing ventricular far field effects may be summarized as follows:
1. R peak detection algorithm is used to identify QRS complexes on one of the BS ECG channels (Lead II or V2).
2. Extract unipolar beats recorded on unipolar IC channel ($UEGM_N$) around R peak detection timestamps.
3. Average all extracted beats to a single mean beat.
4. Cross correlate extracted beats with their average to determine a measure of similarity between the extracted beat and the single mean beat as a function of a time-lag (Template).
5. Align & Select: Align extracted beats in relation according to cross correlation to mean beat peak location.
6. Accept beats in case cross correlation maximum lag is smaller than 10 ms & cross correlation peak amplitude exceeds 90%, i.e., the differences between the peak amplitudes of the mean beat and the extracted beats are less than 10%.
7. Recalculate average on aligned and accepted beat.
8. Construct estimated VFF projection on $UEGM_n$ by duplicating beat at each R peak detection timestamp.
9. Reduce estimated VFF from $UEGM_n$ channel by subtracting $VFF'_{est}$ from unipolar channel.

Run steps 2-9 on all UEGM channels.

Figure 2:
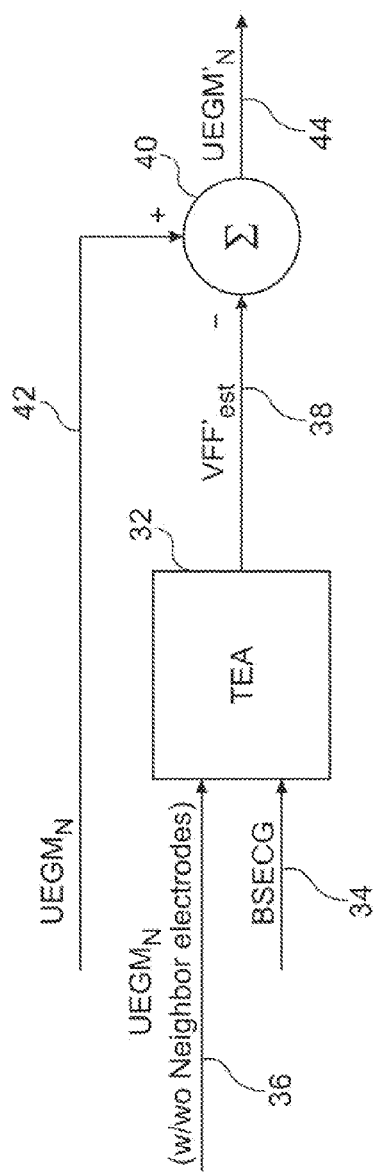
FIG. 2 is a block diagram illustrating removal of ventricular far field effects from intracardiac unipolar channels, in accordance with an embodiment of the invention.

Reference is now made to FIG. 2, which is a block diagram illustrating removal of ventricular far field effects from intracardiac unipolar channels, in accordance with an embodiment of the invention. FIG. 2 and other drawing figures herein show a number of separate functional blocks. These blocks may represent physical entities that conduct the indicated actions, e.g., electronic logical circuitry or a digital signal processor. Alternatively, the blocks may represent different computing tasks or data objects stored in a memory that is accessible to a processor such as the processor 22 (FIG. 1). These tasks may be carried out in software running on a single processor, or on multiple processors. The software may be provided to the processor or processors on tangible non-transitory media, such as CD-ROM or non-volatile memory.

The sequence shown in FIG. 2 is repeated for each relevant electrode in a mapping catheter having multiple electrodes. Block 32 represents a process referred to herein as the time ensemble averaging algorithm (TEA), which accepts two input signals: a first input 34, from another ECG channel, typically but not necessarily a body surface ECG channel (BSECG), and a second input 36, which is a unipolar intracardiac electrode signal ($UEGM_n$). The other ECG channel could be, for example, an esophageal ECG lead, or even another intracardiac catheter ECG. The input 36 may comprise signals from more than one neighboring electrode on the catheter. Templates are created by accumulating, signals from multiple electrodes. Typically 500-600 beats are evaluated. Using multiple electrodes concurrently saves time and increases accuracy. Neighboring electrodes are typically within 2-4 mm of one another. However, the distances are not critical. The block 32 has an estimated ventricular far field output 38 ($VFF'_{est}$), which is an estimate of the ventricular far field component of the input 36. Block 40 is an adder, which subtracts the output 38 from an input 42. The block 40 outputs a filtered version of the input 42 as signal 44, substantially free of ventricular far field effects.

Figure 3:
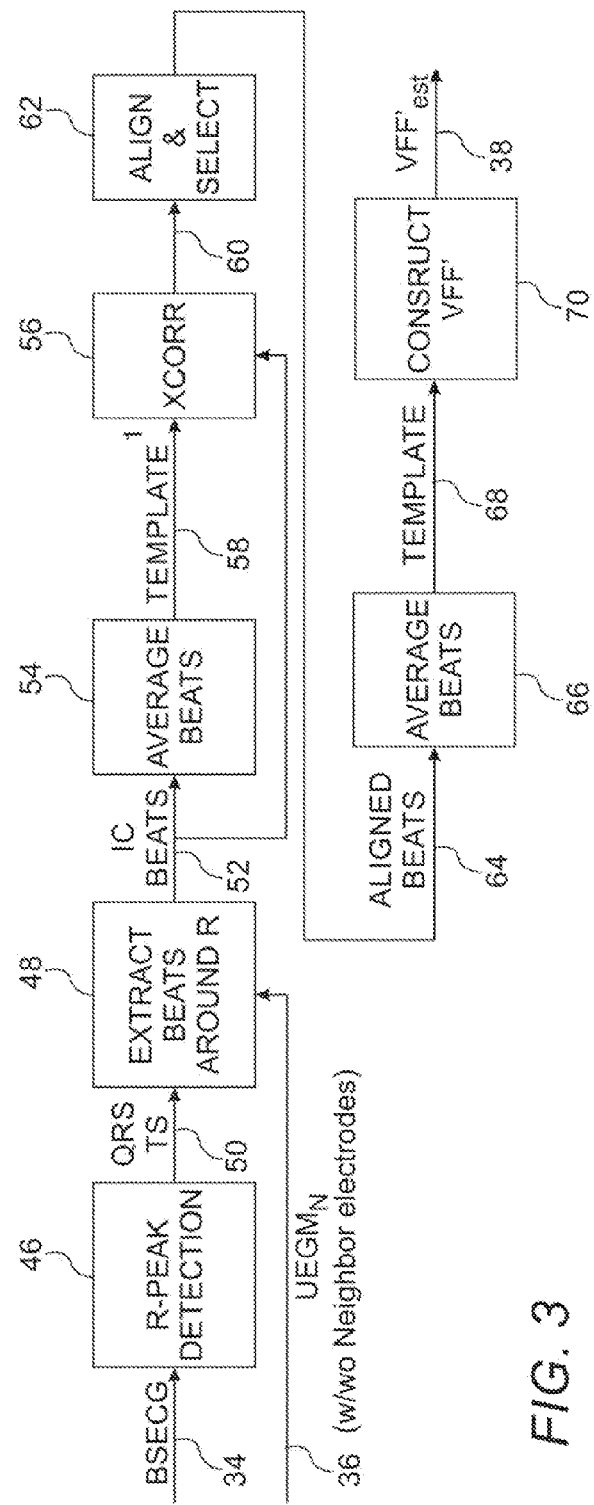
FIG. 3 is a detailed block diagram of the TEA algorithm shown in FIG. 2 in accordance with an embodiment of the invention.

Reference is now made to FIG. 3, which is a detailed block diagram of the TEA algorithm shown in block 32 (FIG. 2) in accordance with an embodiment of the invention. The procedure begins in block 46 with detection of an R-wave peak in the BSECG input 34. R-wave complexes are time-stamped based on the peak detection and are passed to block 48. This transfer is represented as a time-stamp signal 50.

Block 48 accepts the time-stamp signal 50 and the $UEGM_n$ input 36. Beats of the $UEGM_n$ channel are extracted, using the time-stamp signal 50 as a reference. Block 48 outputs an intracardiac electrode signal 52, which forms an input to blocks 54, 56.

Several intracardiac beats are averaged in block 54, which produces a template signal 58 that consists of a moving average of the last m intracardiac beats that represents the moving average. The value of m may be configured by the operator. Averaging the beats over a 30 sec time interval is suitable.

The beats in the intracardiac electrode signal 52 are correlated with the template signal 58 in block 56, which outputs an intracardiac electrode signal 60 that includes correlation information. Signals having a high correlation with the template signal 58 are retained and aligned with the template to obtain the best correlation in a range of −3 to +3 ms. Signals failing to show a high correlation are discarded.

The intracardiac electrode signal 60 is input to block 62, which aligns and selects intracardiac beats for further processing. In block 62 beats failing to show ventricular activity, i.e., ventricular far field activity are rejected as they correlate poorly with the template signal 58. The rejected beats typically only show atrial activity. Block 62 outputs an intracardiac beat signal 64 that is highly correlated with the template signal 58.

The intracardiac beat signal 64 is an input to block 66, which produces a moving average of the last n intracardiac beats and outputs a template signal 68 that represents a moving average of the beats that were selected in block 62. The value of n is configurable. Typically the value n represents beats selected from 30 sec of cardiac activity.

A time-varying signal that estimates the ventricular far field component of the $UEGM_n$ input 36 is generated in block 70 and is output as the estimated ventricular far field output 38.

Second Embodiment

Another embodiment of a time ensemble averaging (TEA) algorithm for removing ventricular far field effects may be summarized as follows:

1. Extract unipolar beats recorded on unipolar IC channel (UEGMN) and its neighboring electrodes around R peak detection timestamps.
2. Mean average all extracted beats from electrode N to a single beat to generate base template.
3. Calculate median filter on all extracted beats derivatives from Electrode N and its neighboring electrodes.
4. Calculate the Cross correlation between all extracted beats derivatives and the median derivative template.
5. Reject all beats that are blow correlation threshold.
6. Operate k-Means algorithm to divide the remaining beats into k clusters based on the Euclidean distance between them.
7. Mean average each cluster beats to k templates.
8. Select best template for VFF reduction per each beat in Electrode N based on cross correlation with template & minimum RM after reduction with template.
9. Use the selected template to construct the estimated ($VFF'_{est}$) signal for reduction.
10. Reduce estimated VFF from UEGMN channel by subtracting $VFF'_{est}$ from unipolar channel.

Reference is now made to FIG. 4, which is a block diagram illustrating removal of ventricular far field effects from intracardiac unipolar channels, in accordance with an alternate embodiment of the invention. Some of the signals indicated in FIG. 5 are identical to those of FIG. 3. Details of these signals are not repeated in the interest of brevity.

A version of the time ensemble averaging is performed in block 72, which accepts the input 36 and the time-stamp signal 50 (FIG. 3). The output of block 72 is an estimated ventricular far field signal 74, which is subtracted from the input 42 (FIG. 3) in block 76 (10Σ). The block 76 outputs a filtered version of the input 42 as signal 78, substantially free of ventricular far field effects.

Reference is now made to FIG. 5, which is a detailed block diagram of the TEA algorithm shown in block 72 (FIG. 4) in accordance with an alternate embodiment of the invention. Block 80 accepts time-stamp signal 50 and input 36 as described above. Beats of the $UEGM_n$ channel are extracted. However, there are now two outputs: (1) a signal 82 constitutes intracardiac beats from a single electrode selected from the input 36. It will be recalled that the input 36 may employ signals from more than one neighboring electrode on the catheter; and (2) a signal 84 constituting intracardiac beats from nine neighboring electrodes centered about the electrode selected for the signal 82. The components of the signal 84 attributable to respective electrodes may be communicated sequentially or concurrently, using any suitable communication protocol.

The signal 82 is subjected to mean averaging in block 86 to form a template signal 88. The template signal 88 is processed in block 110, which is described below. Typically the template signal 88 represents an average of all beats of one electrode during a recording interval, and typically comprises about 500 beats.

The signal 84 is differentiated with respect to time and the derivatives of each of the nine electrodes subjected to median averaging in block 90. A median template signal 92 generated from the median averaging process is output from the block 90.

The derivatives that are output as the median template signal 92 are correlated with respective intracardiac beats of the electrode signal 84 in block 94. The correlation involves squaring the signals from each of the 9 electrodes. Correlation results are output as signal 96 to block 98, where intracardiac beats having a correlation coefficient that is below a predefined threshold are dropped. Such poorly correlated beats typically have a high component of atrial activity and are undesirable for obtaining an isolated ventricular far field component. The remaining intracardiac beats of the signal 84 are output as signal 100.

The signal 100 is an input to block 102 where the filtered intracardiac beats are classified into k groups using k-means clustering, each group being 50 ms in duration. The value of k is 3 in a current embodiment. K-means clustering is a partitioning method that partitions observed data into k mutually exclusive clusters using the Euclidean distance as a metric, and returns the index of the cluster to which it has assigned each observation. The k groups are output as a k-cluster signal 104. A mean is calculated for each of the k groups in block 106. K templates and the individual filtered beats are output as a signal 108.

The k-template signal 108 and the template signal 88 along with the individual beats and their cluster assignments are input to a selection block 110 where each filtered beat is associated with the most suitable one of the k templates of the k-template signal 108 or the template signal 88 and output as signal 112. A ventricular far field estimate is developed on a per beat basis in block 114 using the signal 112 and output as the estimated ventricular far field signal 74, where it is processed in block 76 (FIG. 5).

Reference is now made to FIG. 6-FIG. 15, which are diagrams of waveforms that may be observed when performing the method of FIG. 4 and FIG. 5, in accordance with an embodiment of the invention.

Figure 6:
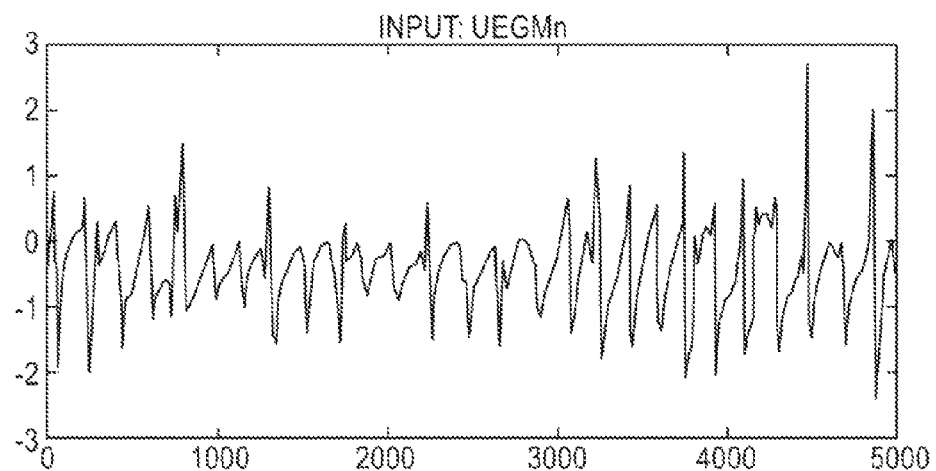
FIG. 6-FIG. 15 are diagrams of waveforms that may be observed when performing the method shown in FIG. 4 and FIG. 5 in accordance with an alternate embodiment of the invention.

FIG. 6 represents a single intracardiac electrogram ($UEGM_n$) of the input 36.

Figure 7:
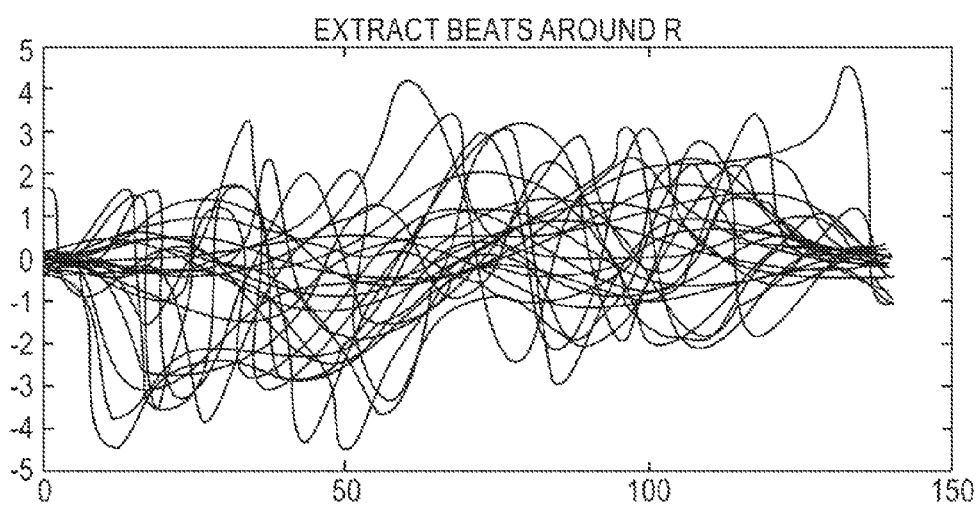

FIG. 7 represents the signal 84 from multiple electrodes, after extraction of beats about the R-wave complex.

Figure 8:
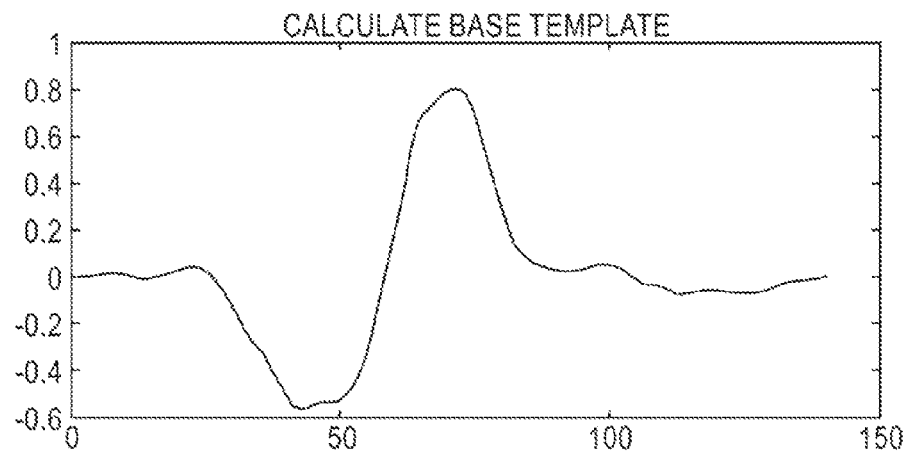

FIG. 8 represents a base template, best appreciated as the template signal 88 (FIG. 5).

Figure 9:
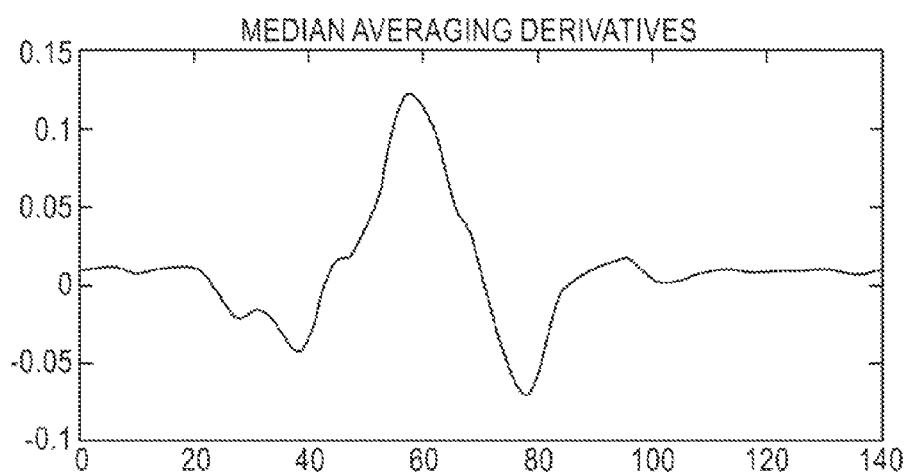

FIG. 9 represents the median template signal 92, which is a template resulting from median averaging of derivatives of the extracted beats produced in block 80.

Figure 10:
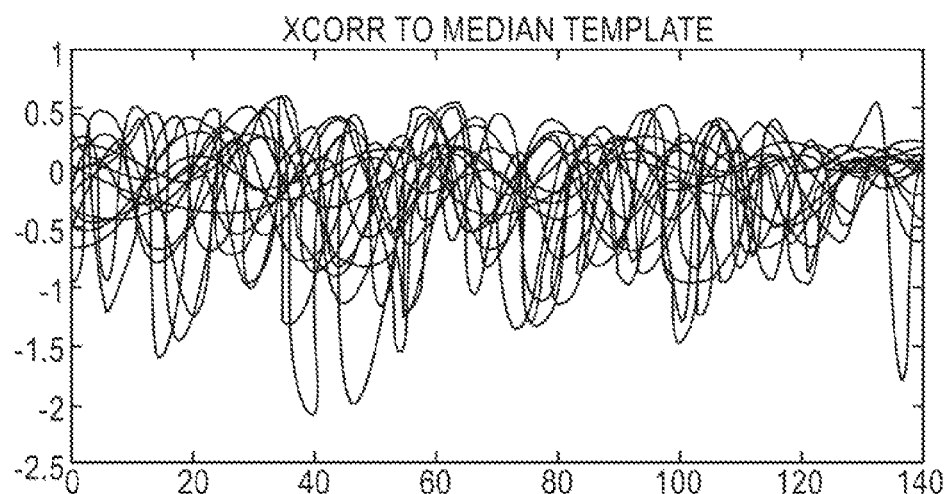

FIG. 10 represents the signal 96, which is the output of the correlation process of block 94.

Figure 11:
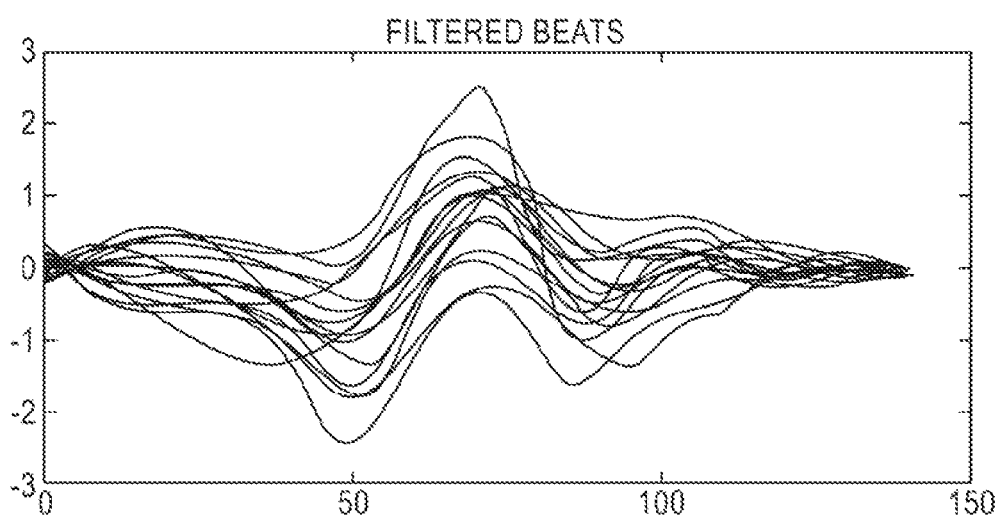

FIG. 11 represents the signal 100, which is the output of the filtering and selection performed in block 98.

Figure 12:
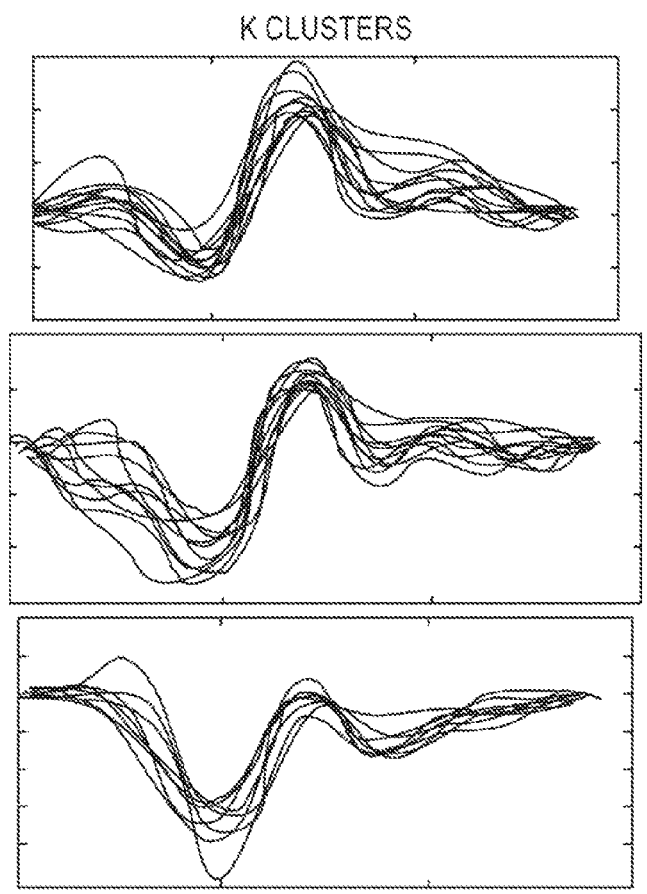

FIG. 12 represents the k-cluster signal 104. It comprises three waveform plots, representing the k-means clustering of the filtered beats that was performed in block 102.

Figure 13:
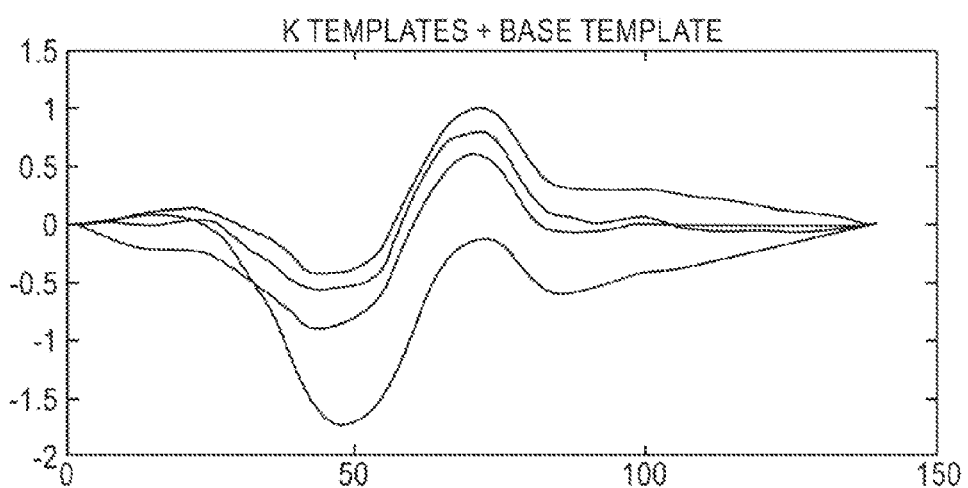

FIG. 13 represents the k-template signal 108, which are three templates formed by block 106 from the k-cluster signal 104.

Figure 14:
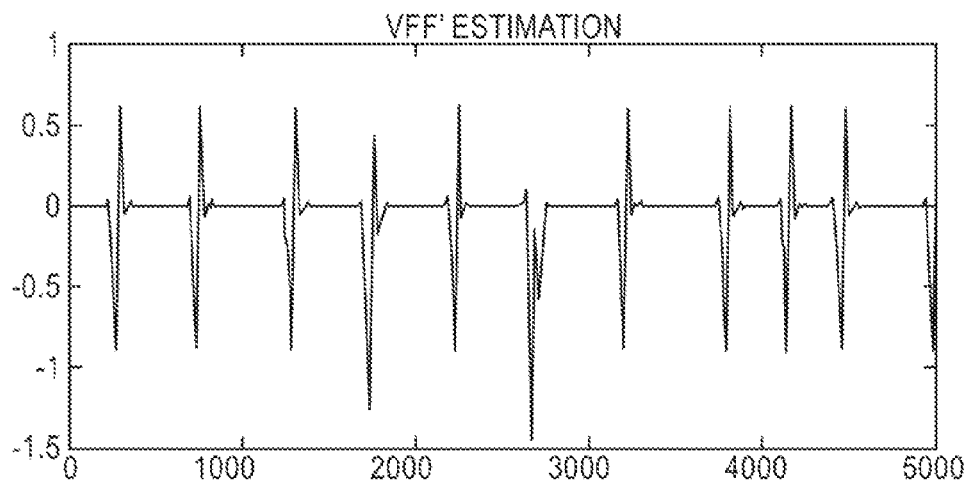

FIG. 14 represents the estimated ventricular far field signal 74 that was generated in block 114.

Figure 15:
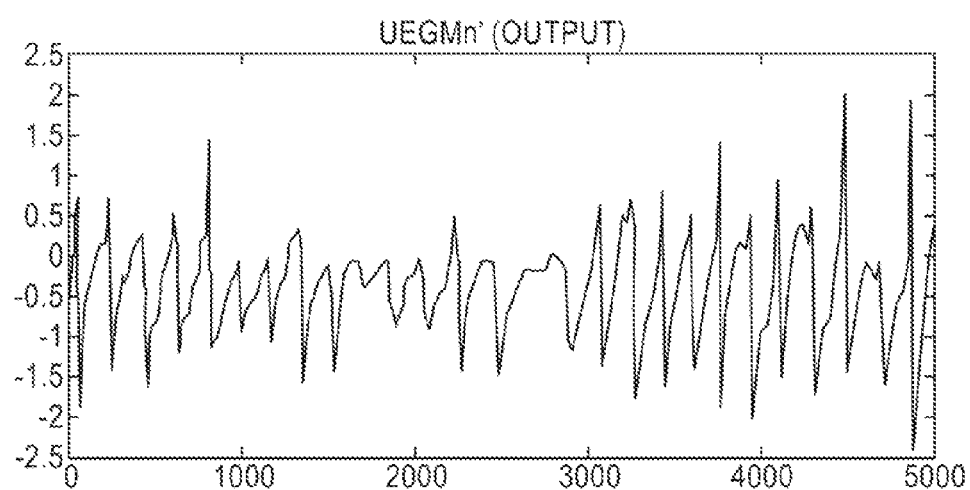

FIG. 15 represents the signal 78, which is the final output: an intracardiac electrogram stripped of a ventricular far field component.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A method of far field reduction, comprising the steps of detecting peaks of a QRS complex of a cardiac electrogram;
   extracting unipolar beats of an intracardiac electrogram that occur within a predetermined time interval that includes respective detected peaks;
   constructing a first mean unipolar beat by averaging the extracted unipolar beats;
   cross correlating the extracted unipolar beats with the first mean unipolar beat by determining respective time-lags therebetween;
   accepting ones of the extracted unipolar beats wherein a cross correlation thereof exceeds a predetermined correlation threshold;
   constructing a second mean unipolar beat from the accepted unipolar beats;
   determining a ventricular far field component by subtracting the second mean unipolar beat from the extracted unipolar beats;
   subtracting the ventricular far field component from the intracardiac electrogram to distinguish a local component of the intracardiac electrogram; and
   controlling a medical procedure responsively to the local component.

2. The method according to claim 1, wherein the predetermined correlation threshold comprises a time lag that does not exceed 10 ms.

3. The method according to claim 1, wherein the predetermined correlation threshold comprises a difference between peak amplitudes of the extracted unipolar beats and the first mean unipolar beat that does not exceed 10 percent.

4. The method according to claim 1, wherein constructing a first mean unipolar beat further comprises computing a median derivative beat by differentiating the extracted unipolar beats, and cross correlating is performed between the extracted unipolar beats and the median derivative beat.

5. The method according to claim 1, wherein constructing a second mean unipolar beat comprises aligning the extracted unipolar beats.

6. The method according to claim 1, wherein constructing a second mean unipolar beat comprises:
   dividing the accepted unipolar beats into a plurality of clusters; and
   constructing respective cluster-specific mean unipolar beats for each of the clusters.

7. The method according to claim 6, wherein dividing the accepted unipolar beats is performed by k-means clustering according to Euclidean distances between the accepted unipolar beats.

8. The method according to claim 6, wherein determining a ventricular far field component comprises:
   selecting an optimum one of the cluster-specific mean unipolar beats for respective accepted unipolar beats; and
   subtracting the selected cluster-specific mean unipolar beats from the extracted unipolar beats.

9. An apparatus, comprising:
   an intra-body probe having an electrode, the probe being configured to contact tissue in a heart;
   one or more body surface electrodes adapted to placed on an outer surface of a subject's body;
   a display; and
   a processor, which is configured to receive a cardiac electrogram signal from the one or more body surface electrodes and which is configured to receive an electrical signal from the electrode, to distinguish a local component, due to the tissue with which the electrode is in contact, in the electrical signal from a remote-field contribution to the signal by performing the steps of:
   detecting peaks of a QRS complex of the cardiac electrogram;
   extracting unipolar beats of an intracardiac electrogram received via the electrode, wherein the extracted unipolar beats occur within a predetermined time interval that includes respective detected peaks;
   constructing a first mean unipolar beat by averaging the extracted unipolar beats;
   cross correlating the extracted unipolar beats with the first mean unipolar beat by determining respective time-lags therebetween;
   accepting ones of the extracted unipolar beats wherein a cross correlation thereof exceeds a predetermined correlation threshold;
   constructing a second mean unipolar beat from the accepted unipolar beats;
   determining a ventricular far field component by subtracting the second mean unipolar beat from the extracted unipolar beats;
   subtracting the ventricular far field component from the intracardiac electrogram to distinguish the local component of the intracardiac electrogram; and
   outputting the local component to the display.

10. The apparatus according to claim 9, wherein the predetermined correlation threshold comprises a time lag that does not exceed 10 ms.

11. The apparatus according to claim 9, wherein the predetermined correlation threshold comprises a difference between peak amplitudes of the extracted unipolar beats and the first mean unipolar beat that does not exceed 10 percent.

12. The apparatus according to claim 9, wherein constructing a first mean unipolar beat further comprises computing a median derivative beat by differentiating the extracted unipolar beats, and cross correlating is performed between the extracted unipolar beats and the median derivative beat.

13. The apparatus according to claim 9, wherein constructing a second mean unipolar beat comprises aligning the extracted unipolar beats.

14. The apparatus according to claim 9, wherein constructing a second mean unipolar beat comprises:
dividing the accepted unipolar beats into a plurality of clusters; and
constructing respective cluster-specific mean unipolar beats for each of the clusters.

15. The apparatus according to claim 14, wherein dividing the accepted unipolar beats is performed by k-means clustering according to Euclidean distances between the accepted unipolar beats.

16. The apparatus according to claim 14, wherein determining a ventricular far field component comprises:
selecting an optimum one of the cluster-specific mean unipolar beats for respective accepted unipolar beats; and
subtracting the selected cluster-specific mean unipolar beats from the extracted unipolar beats, respectively.

* * * * *